(12) United States Patent
Ganey

(10) Patent No.: US 12,616,774 B2
(45) Date of Patent: May 5, 2026

(54) LYOPHILIZED HYDROGEL WOUND DRESSING

(71) Applicant: Bone Pharm, LLC, Tampa, FL (US)

(72) Inventor: Timothy Ganey, Tampa, FL (US)

(73) Assignee: Bone Pharm, LLC, Tampa, FL (US)

( * ) Notice: Subject to any disclaimer, the term of this patent is extended or adjusted under 35 U.S.C. 154(b) by 622 days.

(21) Appl. No.: 17/983,010

(22) Filed: Nov. 8, 2022

(65) Prior Publication Data

US 2024/0148934 A1 May 9, 2024

(51) Int. Cl.
*A61L 26/00* (2006.01)

(52) U.S. Cl.
CPC ......... *A61L 26/008* (2013.01); *A61L 26/0033* (2013.01); *A61L 2300/404* (2013.01)

(58) Field of Classification Search
CPC ............. A61L 26/0085; A61L 2300/00; A61L 26/0033; A61L 2300/404; A61L 26/008; A61F 13/00; A61F 13/00008; A61F 13/00021; A61F 2013/00089; A61F 13/00063
See application file for complete search history.

(56) References Cited

U.S. PATENT DOCUMENTS

| | | | |
|---|---|---|---|
| 4,226,232 A | 10/1980 | Spence | |
| 4,772,419 A | 9/1988 | Maelson et al. | |
| 5,106,629 A | 4/1992 | Cartmell et al. | |
| 5,409,703 A | 4/1995 | Mcanalley et al. | |
| 5,695,777 A | 12/1997 | Donovan et al. | |
| 6,203,845 B1 | 3/2001 | Qin et al. | |
| 6,268,405 B1 | 7/2001 | Yao et al. | |
| 8,795,709 B2 | 8/2014 | Sawhney et al. | |
| 10,080,816 B2 * | 9/2018 | Pillay | A61L 15/44 |
| 10,940,231 B2 | 3/2021 | Sawhney et al. | |
| 11,241,516 B2 | 2/2022 | Castro Feo et al. | |

FOREIGN PATENT DOCUMENTS

| | | | | |
|---|---|---|---|---|
| FR | 3035107 A1 * | 10/2016 | | C07K 14/78 |
| WO | WO-2019040729 A1 * | 2/2019 | | A61M 1/90 |

* cited by examiner

*Primary Examiner* — Ophelia A Hawthorne
(74) *Attorney, Agent, or Firm* — David O. Simmons

(57) ABSTRACT

A wound dressing composition having a first layer of a lyophilized hydrogel layer having hydrolyzed collagen and hydrolyzed hyaluronic acid ingredients, wherein the first layer has a water content of 10 percent or less and is configured to lay onto a wound. The first layer can be cut or molded to various shapes such as a rectangle, a square, a polygon, an oval or a circle. The first layer is hermetically sealed in a cover or barrier and placed in final packaging. Alternatively, one or more additional layers are stacked onto the first layer, each additional one or more layers having a water content greater than that of the first layer.

9 Claims, 5 Drawing Sheets

10

10

100 10

100

20 100 20

100 20

10

100

100

100

100

[10% $H_2O$]

[30% $H_2O$]

[50% $H_2O$]

200

[10% $H_2O$]
[30% $H_2O$]
[50% $H_2O$]

Wound

40

Hot seal          Serrated Tear Off

LYOPHILIZED HYDROGEL WOUND DRESSING

TECHNICAL FIELD

The present invention relates to a lyophilized hydrogel wound dressing, more particularly, a multi-layered laminated product.

BACKGROUND OF THE INVENTION

The use of hydrogel wound dressings is well known. Hydrogels are known as water-swollen polymeric materials that maintain a distinct three-dimensional structure. They can be composed of complex hydrophilic polymers and often have a high water content, often as high as 90 percent water. They are among the first biomaterials designed for use in the human body, traditional methods for attaining structural integrity include crosslinking copolymerization, crosslinking of reactive polymer precursors, and crosslinking via polymer-polymer reaction. By definition hydrogels demonstrate a predominance of water. Compositions can include linear polymers, spheroids and may include voids as negative space.

Hydrogel wound dressings are non-adherent and provide moisture to the wound, creating a moist environment that promotes autolytic debridement, granulation and epithelialization. Hydrogels can also absorb moisture from a wound. Based on the material used for their fabrication, hydrogels can be subdivided into two main groups-natural and synthetic.

As described herein, the present invention discloses a unique wound dressing made of a layer or distinct layers varying in water content and fluid absorption capacities.

SUMMARY OF THE INVENTION

A wound dressing composition having a first layer of a lyophilized hydrogel layer having hydrolyzed collagen and hydrolyzed hyaluronic acid ingredients, wherein the first layer has a water content of 10 percent or less and is configured to lay onto a wound. The first layer can be cut or molded to various shapes such as a rectangle, a square, a polygon, an oval or a circle. The first layer is hermetically sealed in a cover or barrier and placed in final packaging.

In another embodiment, a multiple layer wound dressing composition has a first layer of a lyophilized hydrogel layer having hydrolyzed collagen and hydrolyzed hyaluronic acid ingredients, the first layer having a water content of 10 percent or less and configured to lay onto a wound surface, and one or more additional layers of lyophilized hydrogel stacked onto the first layer, each additional one or more layers having a water content greater than that of the first layer.

The composition can further include one or more of a preservative, antimicrobial, anti-fungal, mechanical stabilizer, fragrance, protectant, or elemental metal.

One of the additional layers adjacent the first layer has a water content of 25 percent to 50 percent. Alternatively, one layer of the additional layers has a higher water content of 50 percent to 90 percent.

The composition further has removable interleaved barrier sheets between the layers to prevent degradation of the water content of each layer and wherein one of the additional layers adjacent the first layer has a water content of 25 percent to 50 percent.

Preferably, the layers are made in the absence of hydrogen peroxide.

The removable interleaved barrier sheets between the layers have a tear seam along one of two sides or ends that allows the layers to be removed at the time of use, wherein each layer is cut or molded to various shapes such as rectangles, squares, polygons, ovals or circles.

A method of applying a wound dressing composition has the steps of providing a first layer of a lyophilized hydrogel layer having hydrolyzed collagen and hydrolyzed hyaluronic acid ingredients with a water content of 10 percent or less hermetically sealed in a cover or barrier; removing the cover or barrier; and placing the first layer on a wound surface.

A method of applying a multiple layer wound dressing composition has the steps of providing a first layer of a lyophilized hydrogel layer having hydrolyzed collagen and hydrolyzed hyaluronic acid ingredients with a water content of 10 percent or less; providing one or more additional layers of lyophilized hydrogel stacked onto the first layer with removable interleaved barrier sheets between the layers to prevent degradation of the water content of each layer, each additional one or more layers having a water content greater than that of the first layer; removing the interleaved barrier sheets at a tear seam along one of two sides or ends of the interleaved barrier sheets; and pulling the interleaved barrier sheets apart and away from the layers allowing the layers to lie on top of one another over a wound surface.

BRIEF DESCRIPTION OF THE DRAWINGS

The invention will be described by way of example and with reference to the accompanying drawings in which.

DETAILED DESCRIPTION OF THE INVENTION

With reference to FIGS. 1-3 and 6, hydrogel 10 is manufactured with water content up to 90%. The sheet product 100 is lyophilized to achieve ranges from less than 10% water content up to 90%.

Figure 1:
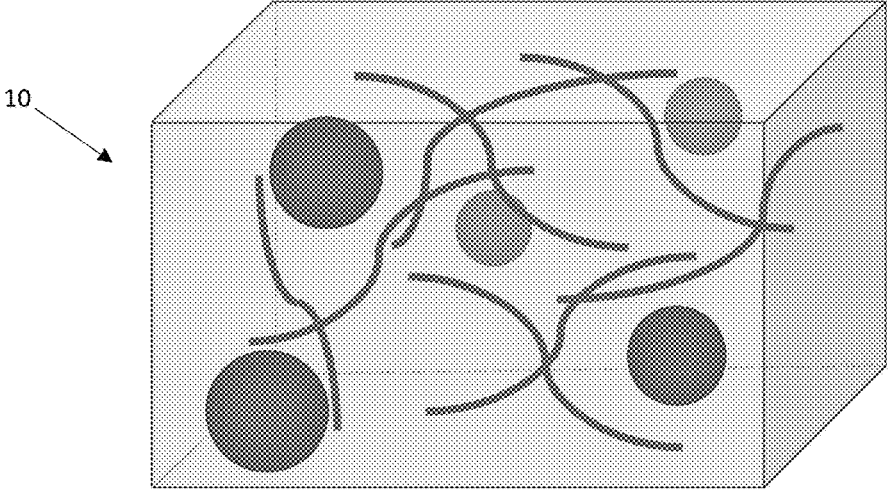
FIG. 1 is an exemplary depiction of a hydrogel composition of the present invention in the form of a rectangular structure.
Figure 2:
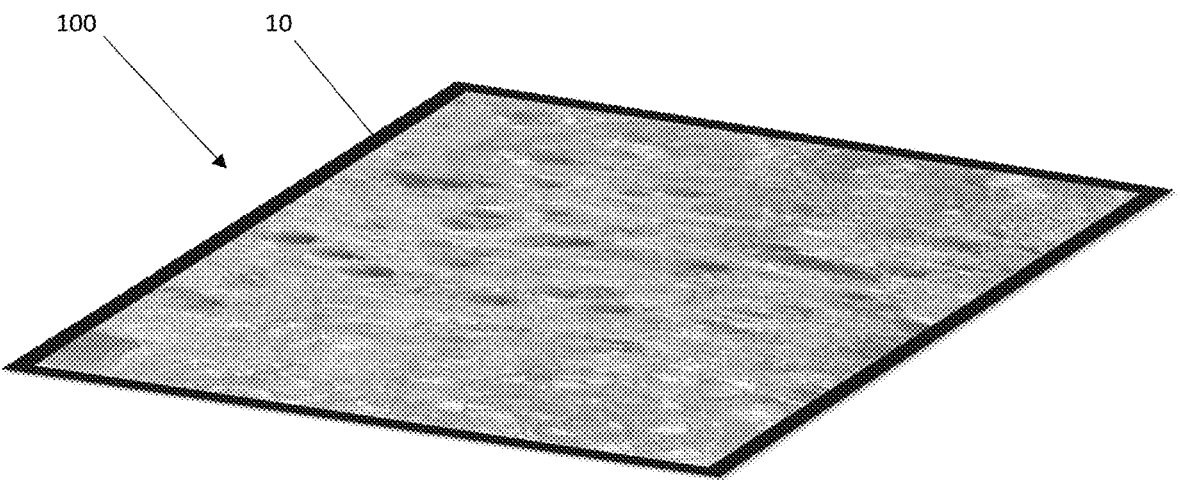
FIG. 2 is an exemplary depiction of the lyophilized hydrogel composition of FIG. 1 shown as a flattened sheet after lyophilization.
Figure 3:
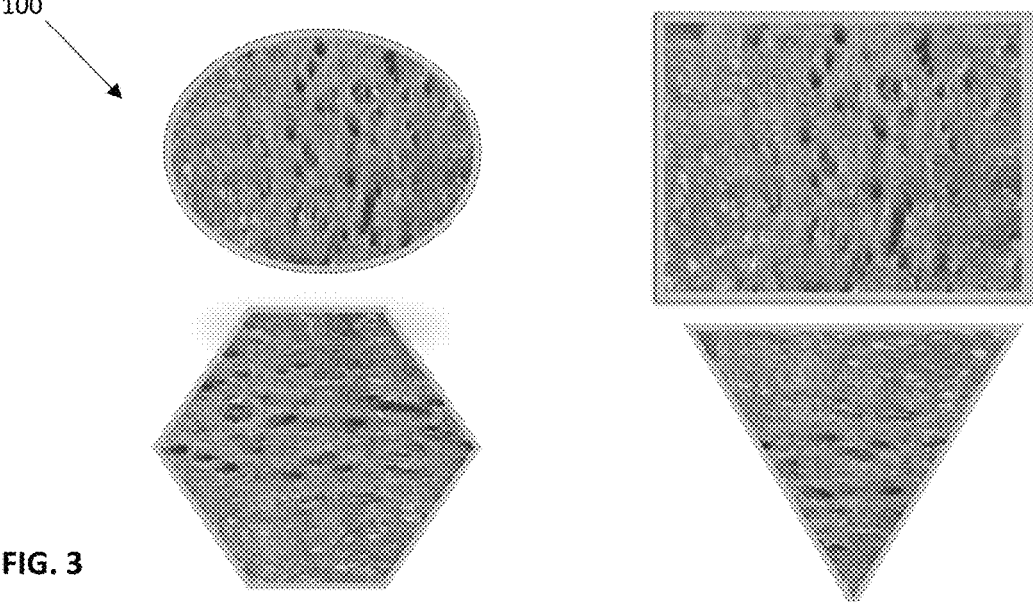
FIG. 3 is an exemplary depiction of various shapes in which the lyophilized hydrogel can be formed.

With reference to FIG. 3, the sheet product 100 is shown in various shapes to accommodate the intended use.

Figure 4:
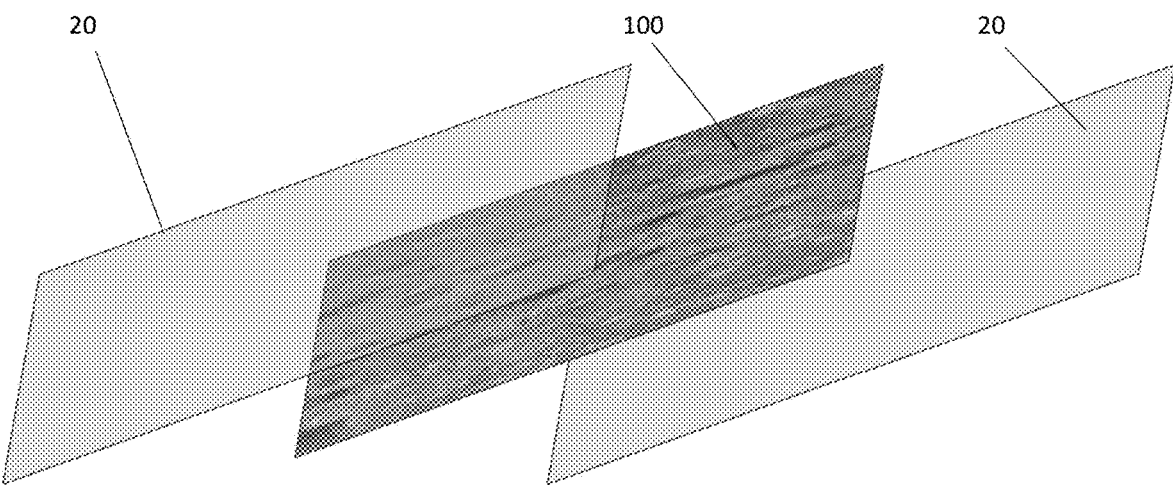
FIG. 4 is a depiction of the lyophilized hydrogel with a covering applied to seal the hydrogel dressing.
Figure 5:
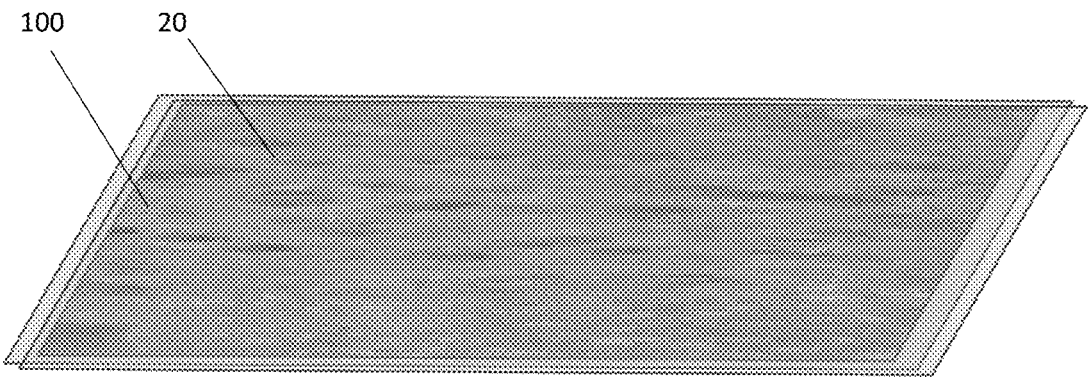
FIG. 5 shows the hydrogel dressing of FIG. 4 after being hermetically sealed.
Figure 6:
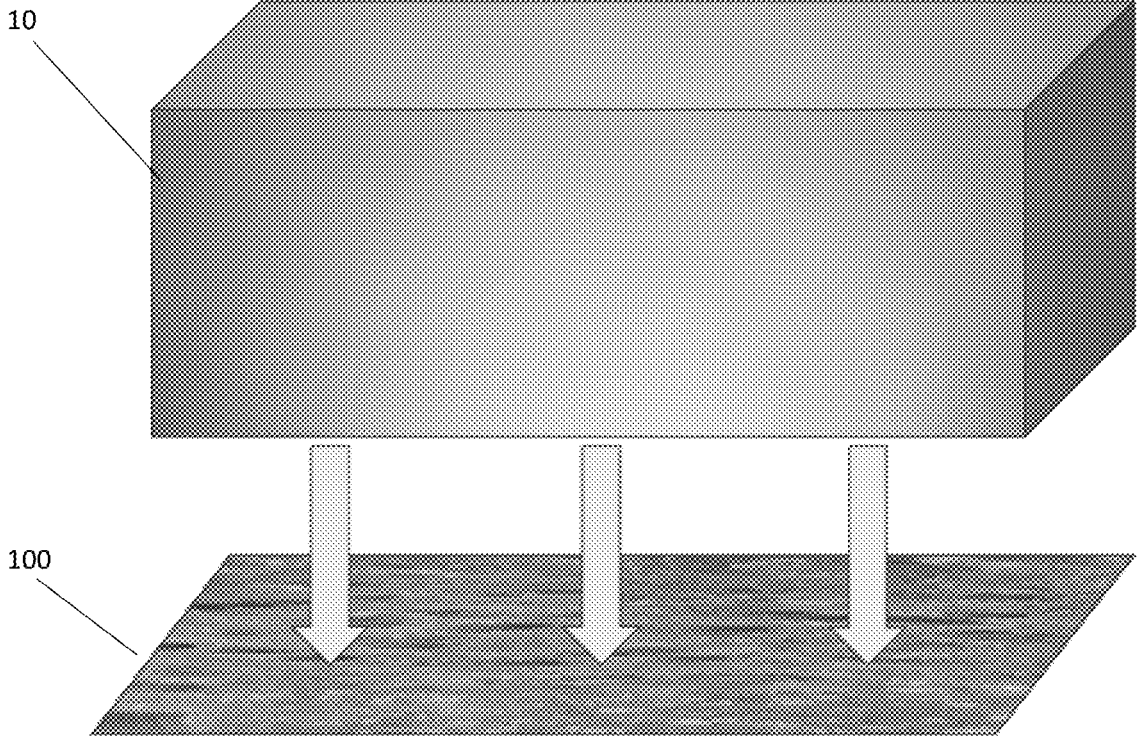
FIG. 6 shows an exemplary depiction of the water concentration of the hydrogel composition before and after lyophilization.

FIGS. 4 and 5 illustrate the covering or hermetic sealing used to package and preserve the hydrogel until the time of use.

By way of example, the ingredients of the original composition will have increased as the reciprocal from 10% maximum in the original composition to a final product concentration that is nine-fold relative to the original preparation. In other words, 90% of the water content has been removed.

Antimicrobial and antiseptic activity achieve greater concentration at the wound surface than during the manufacturing of the hydrogel.

Wound exudate, including bacterial flora, absorbed into the sheet dressing 100 will be countered by high concentration in early application, and achieve and sustain a concentration at least as high as the original concentration achieved during manufacturing.

Figure 7:
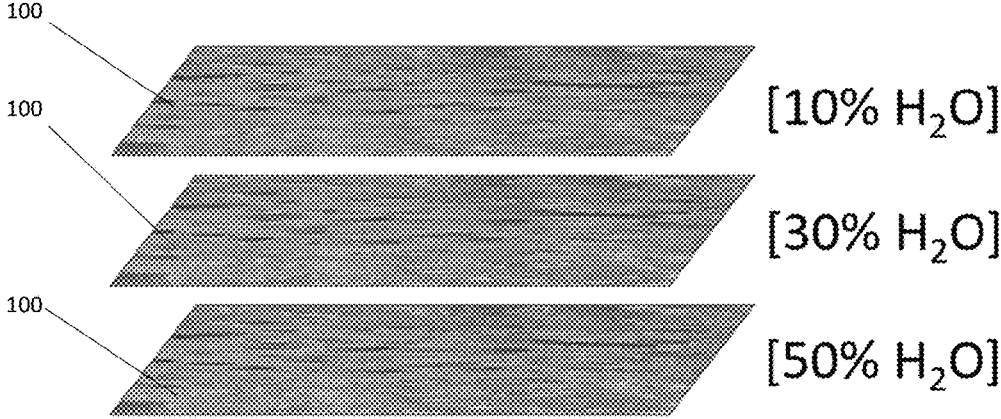
FIG. 7 is an exemplary depiction of three lyophilized hydrogel dressings with 10, 30 and 50 percent water concentrations.
Figure 8:
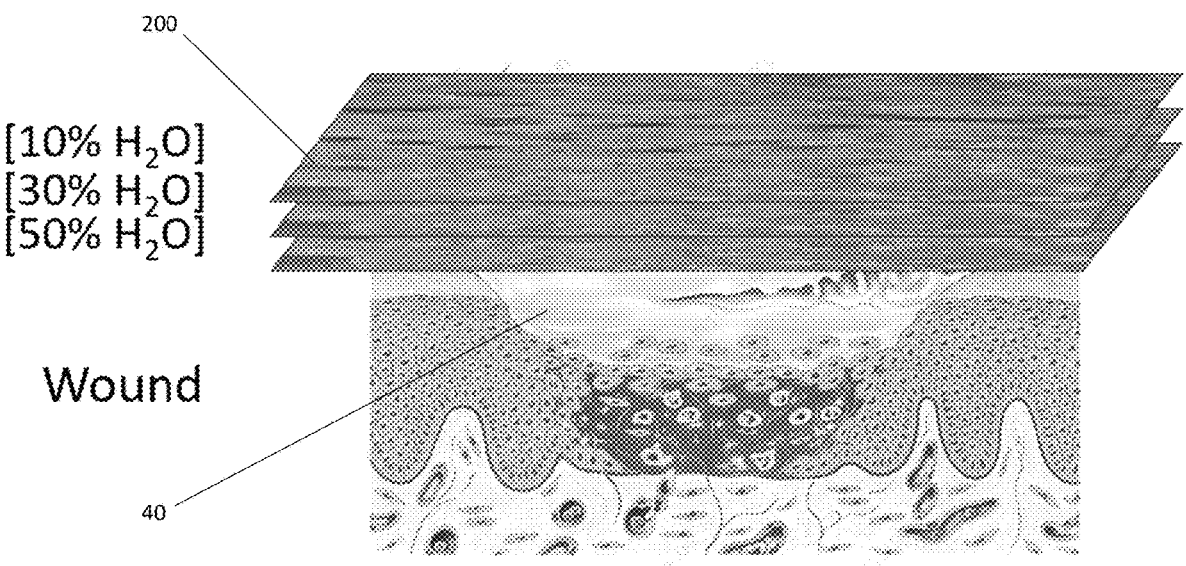
FIG. 8 is an exemplary depiction of a wound covered with a laminated hydrogel dressing composed of three layers of hydrogel with 10, 30 and 50 percent water concentrations shown separated for illustration purposes.

Composition Laminate products 200 are stacked to have the higher water content at wound surface 40. Numbers listed and shown in the figures are graded as example, but not limited to proportion. Stacked composition product 200 of laminates 100 of 10, 30 and 50 percent $H_2O$ are shown in FIGS. 7 and 8. This provides intermediate water concentration mid-substance and lowest water content with highest ingredient content at the wound surface 40.

The laminate composition product 200 is constructed to accentuate diffusion of highest concentration to lower concentration and to accentuate material concentration across a water gradient. Water gradient is structured and imposed in dressing 200 to retain a reserve concentration that is wicked from a reservoir that is conceived in concentration and desiccation dependent.

Figure 9:
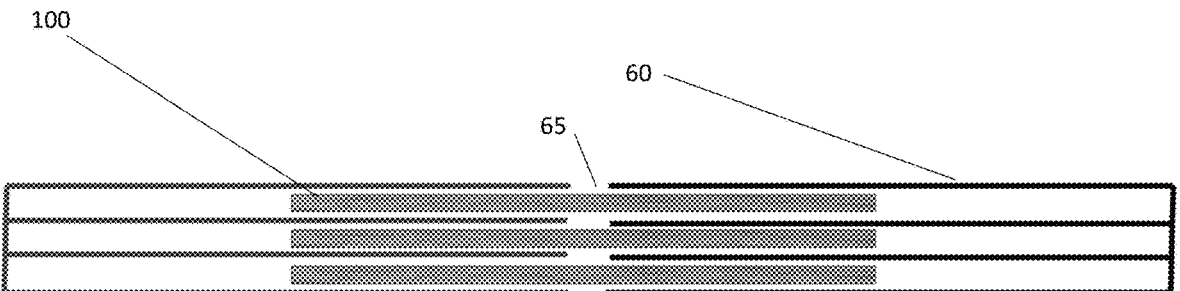
FIG. 9 is an illustration of an end view of the hydrogel wound dressing of the present invention in a sliding interleaved packaging.
Figure 10:
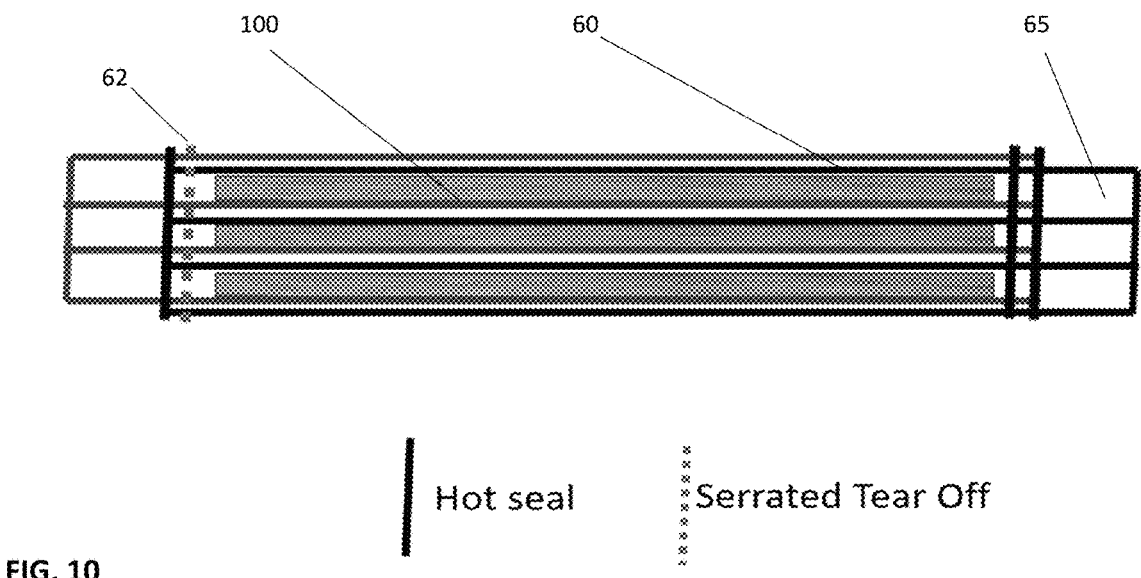
FIG. 10 is taken from FIG. 9 showing the packaging slid together.

The example shown is for 3 layers but is not restricted to lamina of only 3 layers. As shown in FIGS. 9 and 10, each moisture level is sealed to preserve percentages until time of use. Each interleave 65 in the packaging 60 is thermally soldered or melted to create a multi-chamber stack. A serrated edge 62 is used to allow for breaking bonds of separation in the packaging.

At the time of application or use on a wound, the edge of the packaging 60 is torn, both loose ends of the laminate cover 20 extending beyond the graft 100 are grasped and pinched, then the laminate cover 20 is gently pulled to allow the graft 100 to release. The graft 100 is then applied to a wound. When using a single layer dressing 100, the layer has a low water content of 10% or less.

The unique feature of the present invention is to place adjacent materials in proximity that can utilize and siphon higher concentrations to the wound surface. The intentions are 3-fold; to provide hydration and an antiseptic hydrogel to the wound, to offer a convenient sheet-based delivery system for deploying and applying and to align a novel delivery system that uses processes such as diffusion to maintain a high level of active ingredients without the need for multiple changes over brief periods which is also a convenience factor.

The novelty of the wound dressing 100, 200 is not simply the dehydration of a material, but of the use of dehydration to create deliverable protection and healing for wounds as they are rehydrated with wound exudate or with saline during treatment. The concepts of Dehydration and Lyophilization are processes by which water is removed to create a dried product that is shelf stable at room temperature. This is accomplished by evaporative drying or freeze-drying, the differences are in process rather than in the final goal.

Lyophilization, also known as freeze-drying, is a process in which water is removed from a product after it is frozen and placed under a vacuum, allowing the ice to change directly from solid to vapor without passing through a liquid phase. This is the basis for the wound dressing sheet 100 and multi-ply products 200. A condenser traps the migrating vapor molecules in the form of ice on its surface to ensure that they are not allowed to enter the vacuum pump.

Cycle Recipes include the input parameters such as temperature, pressure and time required for the equipment perform lyophilization; each recipe consists of multiple steps involving for both freezing and drying of the product. The art of building the product is critical and aligns equipment controls that assure predictable vacuum and moisture content, temperature and pressure, and logged performance for quality assurance and product optimization. Definitions below characterize key variables that are maintained in record for review and refinement.

Vacuum C or Vacuum Capacitance measures the absolute pressure within the freeze-dryer chamber.

Vacuum P or Vacuum Pirani measures the pressure, including water vapor pressure within the freeze-dryer chamber.

Vacuum System, for the freeze-drying process to work, a vacuum must be created to provide the conditions where water can only exist as a solid or gas.

Tissue and collagen bio-scaffolds have become a unique yet vital part of various medical specialties, especially emergency medicine. The ever-evolving field of wound care in particular relies on these and hydrogel scaffolds to change and save lives. The present process is unique and aligns a synthetic option to create the hydrogel and a manufacturing process that selectively enhances the interface of wound and treatment to sustain the healing effect. Once this invaluable raw material is manufactured and built, it must be stabilized for preservation, transport, and long-term storage.

Freeze-drying is crucial as it accomplishes all this without any degradation to the hydrogel composition, honoring the value of the molecules that offer antimicrobial protection, pH balance, and improved wound healing. Novel to present concept is the multi-ply context of identical composition with varying levels of hydration.

Tissue freeze-drying presents unique challenges due to the broad variation in the content and form of materials as well as the various containers used to handle and store the product. To develop a consistent and optimized freeze-drying process for tissues, the relationship between the application, the equipment, and three steps of freeze drying needs to be fully considered. Common challenges for efficient wound sheet preparation include the Tissue Container and shelf contact vs. non-shelf contact. Starting from a hydrogel semi-solid colloid, allows the process to accommodate a variety of containers that have been used for tissue freeze drying. Challenges to the process of freeze-drying tissues are met with the compositional consistency that are further addressed in the overall design of the lyophilizer.

Although various materials have been used, a sandwich style stainless-steel packing allows for uniform thickness and direct and uniform contact with the lyophilizer shelf, and the limiting dimension used to flatten to the tray. Plastic trays can make heat transfer from the lyophilizer shelf more difficult, resulting in more complex considerations for optimal freezing and sublimation. Metal is used throughout the process to assure efficiency and ergonomics for the equipment performance.

Condensing Rate and Recovery are also critical factors. Freeze drying methods for collagen and tissue vary by application resulting in numerous freeze-drying equipment considerations. Collagen products require units with higher condensing rates due to its high-water content, whereas other tissue-based freeze drying typically involves larger shelf surface area considerations.

Initiating the drying from a colloid state requires a that the combined surface area and moisture need to have a higher condensing rate to sustain the transition from hydrogel to wound sheet: for this application, a large condenser is coupled to a higher condensing rate. For example, the freeze-drying process has a 50 L condenser and condensing rate of 40 L in 24 hours with a highly robust refrigeration system and exposed coil condenser. This drying regimen was established to efficiently handle varying moisture content and large surface areas.

Shelf Size/Spacing is also a consideration. Applications where materials are very thin may work best in a chamber with close shelves. A large number of shelves, a thin sheet product, and the longer goal of casting materials to shapes define a product. Controls within the production include a capacity to measure vacuum, moisture, and temperature. Specifically critical to this product, moisture content is a critical asset to a varying ply stacked product 200.

Multiple layer composition 200 is achieved with sheets individually produced from a bulk composition and dehydrated to a specific moisture level at defined pressure, temperature, and vacuum. Current variables include hydrations ranging from: 40-50% as the foundation, 20-30% as the middle, and 6-10% as the surface layer. Individual plies 100 are stacked with interleaving insulators 62 that separate the layers and prevent neutralization of differences in hydration.

Packaging is novel to this manufacturing process and allows a tearing of a serrated edge 62 to allow the interleaves 65 to be withdrawn prior to placement on the wound 40. When at least one side of the packaging 60 is torn at the serrated edge 62 and pulled apart, the layers 100 come together forming the multiple layer wound dressing 200.

Other iterations, as previously discussed, can include single sheets 100 of the dried hydrogel ranging from 6%-50% depending on wound to be treated.

With reference to processing, Hydrogel 10 is manufactured with hydrolyzed collagen and hydrolyzed hyaluronic acid and other active and inert ingredients. Other ingredients can include preservatives, antimicrobials, anti-fungal, mechanical stabilizers, fragrances, protectants, elemental metals such as gold, silver, zinc, etc. known for preventing infection.

As preservative for stabilizing against germs, fungi and yeasts, at least one organic acid can be used. Potentially, formic acid, benzoic acid, dehydracetic acid, acetic acid, fumaric acid, 4-hydroxybenzoic acid, hydroxysuccinic acid, lactic acid, propionic acid, salicylic acid, sorbic acid etc., and also salts and mixtures thereof would be considerations but not limitations. Preference is given to benzoic acid, dehydracetic acid, lactic acid and sorbic acid, in particular a mixture thereof. 2-Phenoxyethanol is also suitable as preservative.

The hydrogel can also comprise at least one technical auxiliary, which improves e.g. its mechanical properties. These include softeners, moisture regulators, antioxidants, pH buffers, dyes, binders, surfactants, viscosity improvers.

Among these, collagen, hyaluronic acid, allantoin, chitosan, disaccharides, polymers, polypeptides, charged liposomes, conjugated polymers with magnetic particle, structurally asymmetric particles, time-dependent sacrificial structures to effect prescribed and random porosity, etc. would be suitable considerations As an ascent to developing a pleasant odor and to increase the cosmetic effect on the skin (increase in skin moisture, increase in elasticity, wrinkle smoothing, supplying the skin with essential substances (minerals, vitamins, fatty acids, lipids etc.), the hydrogel can comprise at least one fragrance and/or at least one cosmetic active ingredient which can similarly be controlled for release over controlled conditions such as carvacrol, thymol, camphor, menthol, limonene, citral, cineole and p-cymene, or eugenol. In other studies, the volatiles/inclusion complexes with CDs could be incorporated in a biopolymer matrix as zein, opullulan, semisynthetic polymers such as cellulose acetate, or synthetic polymers such as poly (3-hydroxybutyrate-co-3-hydroxyvalerate) (PHBV) via electrospinning. These polymers have been used for the formation of edible or biodegradable antimicrobial films, as well as porous membranes for packaging or biomedical applications The fragrances include odorants, i.e. uniform, defined chemical compounds with an odor. These include natural aroma substances, nature-identical aroma substances, synthetic aroma substances, aroma extracts, reaction aromas and smoke aromas. Mixtures such as essential oils are also included here.

The cosmetic active ingredients include skin oils, skincare agents and skin protectants, but are innumerous and would be known in the art.

In one embodiment, following formulation of the composition, the gel is poured onto receiving stainless steel shelfs, and the moisture is reduced to 75% moisture content to assure a flattened shape and a more gelled composition. A cover floating stainless steel sheet is place on the 75% sheets and the flattened product is further dehydrated to the specification of the single sheet or the ply variants.

If the finished product is a single sheet 100 or single thickness, the sheet 100 is cut to size and vacuum packed in the cover 60 and prepared for final labeling.

Varied multiple sheets 200 manufactured for final plying remain separate and then are sized, interleaved and stacked in a dry chamber to prevent rehydration.

In the preparation of hydrogel semi-solid colloid, the hydrogel is distributed in defined aliquot to trays to account for consistent thickness after dehydration. Particulars listed demonstrate size capacity, and capability. Shelf area: 15 sq ft to 30 sq ft or 1.394 to 2.787 sqM; shelf assembly: bulk or hydraulic stoppering; shelf temperature range: −70° to +65° C.; shelf heat transfer: hollow fluid filled; shelf size/finish: 18"×24", 316 1 ss, 20 ra or better; condenser temp: −85° C.; condenser capacity: 50 L; condenser rate: 40 L in 24 hours; condenser style: exposed coil, 8" vapor port; defrost: hot gas; compressors, scroll: 5 hp (horse power) 1st stage, 3.5 hp 2nd stage; product sensors: 4 type T thermocouples; vacuum pump: corrosion resistant; vacuum control: Pirani with Solenoid and Needle Valve; option: capacitance manometer with proportional control; control system: pc/plc with software; trays: two per shelf; cabinet: 62"w×44"d×87.5"h; and reduction to 75% liquid and placement of stainless steel tamponades. Further reduction to prescribed moisture level and maintenance until removal, cutting and packaging.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims. The surgical access window described herein encompasses the dimensions presented and any and all variations applicable to the methods and surgical technique described directly or indirectly intended with this device.

What is claimed is:

1. A multiple layer wound dressing composition comprising:

a first layer of a lyophilized hydrogel layer having hydrolyzed collagen and hydrolyzed hyaluronic acid ingredients, the first layer having a water content of 10 percent or less and configured to lay onto a wound surface;

one or more additional layers of lyophilized hydrogel stacked onto the first layer, each additional one or more layers having a water content greater than that of the first layer; and removable interleaved barrier sheets between the layers to prevent degradation of the water content of each layer.

2. The composition of claim 1, wherein a plurality of the additional layers adjacent the first layer has a water content of 25 percent to 50 percent.

3. The composition of claim 2, wherein the removable interleaved barrier sheets between the layers have a tear seam along one of two sides or ends that allows the layers to be removed at the time of use.

4. The composition of claim 1, wherein one of the additional layers adjacent the first layer has a water content of 25 percent to 50 percent.

5. The composition of claim 1, wherein one layer of the additional layers has a higher water content of 50 percent to 90 percent.

6. The composition of claim 1, wherein the removable interleaved barrier sheets between the layers have a tear seam along one of two sides or ends that allows the layers to be removed at the time of use.

7. The composition of claim 1, wherein each layer is cut or molded to various shapes such as rectangles, squares, polygons, ovals or circles.

8. The composition of claim 1, wherein the hydrogel layers further include one or more of a preservative, anti-microbial, anti-fungal, mechanical stabilizer, fragrance, protectant, or elemental metal.

9. A method of applying a multiple layer wound dressing composition comprising the steps of:

providing a first layer of a lyophilized hydrogel layer having hydrolyzed collagen and hydrolyzed hyaluronic acid ingredients with a water content of 10 percent or less;

providing one or more additional layers of lyophilized hydrogel stacked onto the first layer with removable interleaved barrier sheets between the layers to prevent degradation of the water content of each layer, each additional one or more layers having a water content greater than that of the first layer;

removing the interleaved barrier sheets at a tear seam along one of two sides or ends of the interleaved barrier sheets; and pulling the interleaved barrier sheets apart and away from the layers allowing the layers to lie on top of one another over a wound surface.

* * * * *